United States Patent
Puskas et al.

(10) Patent No.: US 9,907,815 B2
(45) Date of Patent: Mar. 6, 2018

(54) METHOD FOR PREPARATION OF FILAMENTS OF POLY(α-LIPOIC ACID) POLYMERS

(71) Applicants: Judit E. Puskas, Akron, OH (US); Emily Q. Rosenthal-Kim, Dublin, OH (US)

(72) Inventors: Judit E. Puskas, Akron, OH (US); Emily Q. Rosenthal-Kim, Dublin, OH (US)

(73) Assignee: The University of Akron, Akron (*) Notice: Subject to any disclaimer, the term of this patent is extended or adjusted under 35 U.S.C. 154(b) by 0 days.

(21) Appl. No.: 14/549,661

(22) Filed: Nov. 21, 2014

(65) Prior Publication Data
US 2015/0139933 A1 May 21, 2015

Related U.S. Application Data

(60) Provisional application No. 61/907,074, filed on Nov. 21, 2013.

(51) Int. Cl.
*A61K 31/795* (2006.01)
*A61K 31/385* (2006.01)

(52) U.S. Cl.
CPC .......... *A61K 31/795* (2013.01); *A61K 31/385* (2013.01)

(58) Field of Classification Search
None
See application file for complete search history.

(56) References Cited

U.S. PATENT DOCUMENTS

| 6,756,354 B2* | 6/2004 | Nelson | A61K 31/385 424/450 |
| 2008/0058406 A1 | 3/2008 | Eidenberger | |
| 2012/0245540 A1* | 9/2012 | Zimnitsky | A61K 31/385 604/319 |

FOREIGN PATENT DOCUMENTS

WO  WO-2011113446 A1 *  9/2011  ............... C07K 7/06

OTHER PUBLICATIONS

Reed "Lipoic Acid", "organic Sulpher Compounds" book 1961, chapter 36.*

(Continued)

*Primary Examiner* — Isis A Ghali
(74) *Attorney, Agent, or Firm* — Renner Kenner Greive Bobak Taylor & Weber

(57) ABSTRACT

A method for the polymerization of α-lipoic acid and α-lipoic acid derivatives includes preparing an α-lipoic formulation, exposing the α-lipoic formulation to an aqueous phase and a gaseous phase at a gas/water interface, and allowing the α-lipoic formulation to polymerize at the gas/water interface to form a poly(α-lipoic acid) polymer. The α-lipoic formulation can be an α-lipoic solution of an α-lipoic solute and an organic solvent miscible with water, and can also be an α-lipoic acid or oligomer or polymer thereof in liquid (typically melt) form.

11 Claims, 4 Drawing Sheets

(56) References Cited

OTHER PUBLICATIONS

Merck Index, 2001, pp. 1060, 9734.*
Atsushi Kisanuki, et al., Ring-Opening Polymerization of Lipoic Acid and Characterization of the Polymer, Journal of Polymer Science, Oct. 5, 2010, pp. 5247-5253, vol. 48, Wiley Periodicals, Inc.
Chul Ho Park, et al., Improved efficacy of appetite suppression by lipoic acid particles prepared by nanocomminution, Drug Development and Industrial Pharmacy, 2009, pp. 1305-1311, vol. 35 Issue 11.
Richard C. Thomas, et al., Disulfide Polymers of DL-a-Lipoic Acid, Jun. 29, 1956, pp. 6148-6149, vol. 78.

* cited by examiner

METHOD FOR PREPARATION OF FILAMENTS OF POLY(α-LIPOIC ACID) POLYMERS

CROSS-REFERENCE TO RELATED APPLICATIONS

The present application claim priority to U.S. Provisional Patent Application Ser. No. 61/907,074, filed Nov. 21, 2013, the entirety of which is incorporated herein by reference.

STATEMENT REGARDING FEDERALLY SPONSORED RESEARCH OR DEVELOPMENT

This invention was made with government support under grant DMR 0804878 awarded by National Science Foundation. The government has certain rights in the invention.

FIELD OF THE INVENTION

The present invention generally relates to the polymerization of α-lipoic acid and α-lipoic acid derivatives.

BACKGROUND OF THE INVENTION

The structure α-lipoic acid, with disulfide ring attached by a four-carbon chain to a carboxylic acid group, provides the molecule with unique biological activity. The amphiphilicity of the molecule allows it to penetrate lipid bilayers, including the blood-brain barrier while remaining limitedly soluble in aqueous environments. α-LA is one of the most powerful biological antioxidants and readily reduces reactive oxidant species in biological systems. Additionally, it plays a vital role in the enzymatic redox systems. The disulfide group readily complexes with metals and is a demonstrated chelating agent. Taking advantage of both the antioxidant and chelating properties, α-LA-palladium complexes are being used to protect against radiation poisoning. Additionally, α-LA supplementation has is commonly given to patients with Alzheimer's disease and diabetic neuropathy.

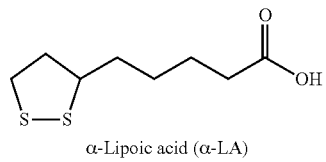 [SMILES: O=C(O)CCCCC1CCSS1]

α-Lipoic acid (α-LA)

α-LA also shows anti-thrombotic properties. One example of exposed α-LA thiolane rings comes from Song and coworkers. Using carbodiimide-activated amidation, α-LA was attached to exposed amine groups on surface of a crosslinked 1,2-diaminocyclohexane coated stent. Platelet adhesion tests using AFM showed that very few platelets adhered to the α-LA-functionalized surfaces compared to the bare metal surface. The authors also discuss that the platelets on the α-LA-functionalized surface are not aggregated and therefore would be less prone to clotting in vivo. These results are supported by a previous study that indicates α-LA inhibits the expression of adhesive molecules in some cells. Platelet adhesion to the crosslinked polymer before α-LA functionalization was not shown.

Redox-sensitive disulfide bonds are an invaluable tool in the design of drug delivery vesicles. The disulfide bond may formed or maintained under mildly oxidizing conditions, such as that found in the slightly basic bloodstream. In reducing environments, such as those found in the cell cytosol and lysosome compartments, disulfide bonds are cleaved to form thiol groups. Disulfide cleavage is accelerated in these environments by enzymes specific to disulfide cleavage. In drug delivery, this means that therapeutic agents maybe trapped in vesicles under mild conditions, continue to be protected while circulating in the body and then be released upon endocytosis. Additionally, crosslinking of self-assembled vesicles, like micelles and liposomes, reduces susceptibility to shear-induced disassembly. The importance of reduction-sensitive vesicles is demonstrated by several review papers.

The resulting reactive thiolate anions formed upon reduction may, however be harmful to the cell. A-LA presents a unique solution to the problem; upon reduction of α-LA crosslinks the resulting dithiolate compound readily reforms the disulfide ring while at the same time reducing a neighboring oxidized species. Separated by four methylene groups from the thiolane ring, the sterically unhindered carboxylic acid group facilitates conjugation to a wide variety of molecules, including peptides, carbohydrate polymers and phospholipids.

Biochemists L. J. Reed and C.-I. Niu first reported the presence of poly(DL-α-LA) in 1955 where it was a byproduct in their synthesis of DL-α-lipoic acid. The following year, Thomas and Reed published an account of the purposeful, thermally-induced polymerization of the disulfide, however the focus of the paper was on the subsequent depolymerization of the polymer to desired DL-α-LA rather than the characterization of the polymer. DL-α-lipoic acid was heated to at 65° C. for fifteen minutes to produce a colorless polymer. The reaction reached monomer conversion of 52%. The next report of α-LA polymerization is from 1980 and used tributylphosphine (TBP) with α-LA in an acetonitrile solution. Rather than polymerize through the disulfide bonds as shown below, this reaction forms poly (thio-1-oxo-6-mercaptooctamethylene) in which the α-LA units are connected via a thioester bond (see below). The pendant thiol group was acetylated to prevent crosslinking through oxidation. Based on polystyrene standards, the number average molecular weight (Mn) of the acetylated polymer was 8,400 g/mol.

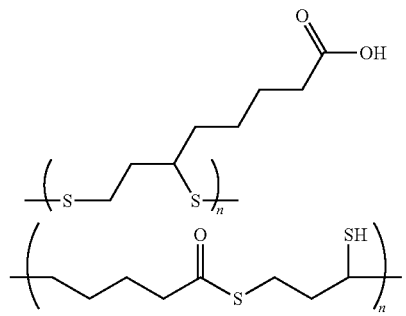

Structure of poly(α-LA) and poly(thio-1-oxo-6-mercaptooctamethylene)

The group of Kiyoshi Endo has been investigating the ring-opening polymerization of cyclic disulfides, including α-LA, for the last decade. Copolymers of α-LA and 1,2-dithiane (DT) of varying molar ratios were thermally polymerized in bulk conditions under high vacuum. Monomer conversion, molecular weights and polydispersity index all increased with increasing α-LA monomer content. An exception to the trend was a slight decrease in Mn for the 100% α-LA homopolymer which reached 416,000 g/mol. The highest molecular weight was found for the 70% α-LA copolymer which had an Mn of 550,000 g/mol (based on polystyrene standards). The authors propose a catenane structure for the copolymers with the interlocking cyclic structures averaging about 5,000 g/mol. These copolymers were later dissolved in pyridine and crosslinked with zinc (II) acetate at room temperature.

Endo and coworkers also investigated the homopolymerization of α-LA on its own. The thermal polymerization was again carried out under high vacuum in bulk conditions. Polymers were not obtained below the melting temperature of the crystalline monomer, but readily polymerized at elevated temperatures with conversion and molecular weight increasing with increasing temperature. Polymers from the reaction carried out at 90° C. reached Mn of 1,370,000 g/mol with a PDI of 1.5 and 66.8% conversion. The catenane structure proposed for the polymer consists of interlocking cyclic polymers of Mn=12,000 g/mol. Their assessment of the cyclic ring stems from the GPC analysis of the UV degradation products of higher molecular weight polymers and from polymerizing α-LA in the presence of cyclic poly(ethylene glycol) derivatives.

SUMMARY OF THE INVENTION

In a first embodiment, the present invention provides a method for the polymerization of α-lipoic acid and α-lipoic acid derivatives. The method comprises preparing an α-lipoic formulation selected from the group consisting of an α-lipoic solution and an α-lipoic liquid of α-lipoic acids, α-lipoic acid based-derivatives, and combinations thereof. The α-lipoic solution is a solution of an α-lipoic solute selected from the group consisting of α-lipoic acids, α-lipoic acid based-derivatives, and combinations thereof and an organic solvent miscible with water. The method further comprises exposing the α-lipoic formulation to an aqueous phase and a gaseous phase at a gas/water interface and allowing the α-lipoic formulation to polymerize at the gas/water interface to form a poly(α-lipoic acid) polymer.

In a second embodiment, the present invention provides a method as in the first embodiment, wherein the α-lipoic formulation is an α-lipoic solution, and the organic solvent is selected from ethanol, isopropanol, methanol, acetone, glycerin, propylene glycol, tetraethylene glycol, dioxane, dimethylsulfoxide and tetrahydrofuran.

In a third embodiment, the present invention provides a method as in any of the embodiments, wherein the α-lipoic formulation is an α-lipoic liquid and further includes oligomers or polymers of α-lipoic acid or α-lipoic acid-containing compounds or both.

In a fourth embodiment, the present invention provides a method as in any of the embodiments, wherein the α-lipoic liquid is liquid due to being heated.

In a fifth embodiment, the present invention provides a method as in any of the embodiments, wherein the α-lipoic formulation includes an ester of α-lipoic acid.

In a sixth embodiment, the present invention provides a method as in any of the embodiments, wherein the ester of α-lipoic acid is produced by an esterification reaction between lipoic acid and a glycol compound.

In a seventh embodiment, the present invention provides a method as in any of the embodiments, wherein the α-lipoic formulation further includes a non-water soluble compound.

In an eighth embodiment, the present invention provides a method as in any of the embodiments, wherein the non-water soluble compound is a therapeutic agent.

In a ninth embodiment, the present invention provides a method as in any of the embodiments, wherein the non-water soluble compound is a crosslinking agent.

In a tenth embodiment, the present invention provides a method as in any of the embodiments, wherein the aqueous phase is selected from the group consisting of water, deionized water, water-based solutions, plasma, saliva, hydrogen peroxide, and aqueous solutions.

In an eleventh embodiment, the present invention provides a method as in any of the embodiments, wherein the aqueous phase is provided by plasma.

In a twelfth embodiment, the present invention provides a method as in any of the embodiments, further comprising wherein the plasma is present in a wound.

In a thirteenth embodiment, the present invention provides a as in any of the embodiments, wherein the aqueous phase contains a water-soluble compound.

In a fourteenth embodiment, the present invention provides a method as in any of the embodiments, wherein the water soluble compound is a therapeutic agent.

In a fifteenth embodiment, the present invention provides a method as in any of the embodiments, wherein the therapeutic agent is selected from the group consisting of water soluble analgesics, acetylsalicylic acid, water soluble vitamins, ascorbic acid, water soluble antibacterial agents, sulfonamides and neomycin B.

In a sixteenth embodiment, the present invention provides a method as in any of the embodiments, wherein the gaseous phase is air.

In a seventeenth embodiment, the present invention provides a method as in any of the embodiments, wherein the gaseous phase is an inert atmosphere.

In an eighteenth embodiment, the present invention provides a method as in any of the embodiments, wherein the gaseous phase is pure oxygen.

In a nineteenth embodiment, the present invention provides a method as in any of the embodiments, wherein, in the step of exposing, the α-lipoic formulation is deposited onto a substrate surface having water thereon.

In a twentieth embodiment, the present invention provides a method as in any of the embodiments, wherein, in the step of exposing, the α-lipoic formulation is deposited onto a second surface having water thereon, the second surface separated from the substrate surface by a gap, and wherein, in the step of allowing the α-lipoic formulation to polymerize, the poly(α-lipoic acid) polymer bridges the gap and helps to hold the substrate surface and the second surface in proximity to each other.

In a twenty-first embodiment, the present invention provides a method as in any of the embodiments, wherein the substrate surface and the second surface are the surfaces of a skin at a wound site.

In a twenty-second embodiment, the present invention provides a method as in any of the embodiments, wherein, in the step of exposing, the α-lipoic formulation is deposited onto water.

In a twenty-third embodiment, the present invention provides a method as in any of the embodiments, wherein, in the step of exposing, the α-lipoic formulation is atomized and deposited onto the gas/water interface.

In a twenty-fourth embodiment, the present invention provides a method as in any of the embodiments, wherein the α-lipoic formulation is atomized and deposited by a 3-D printing device.

In a twenty-fifth embodiment, the present invention provides a method as in any of the embodiments, wherein, in the step of exposing, the α-lipoic formulation is electrosprayed or electrospun onto a gas/water interface.

In a twenty-sixth embodiment, the present invention provides a method as in any of the embodiments, wherein, in the step of exposing, the α-lipoic formulation is subjected to coaxial electrospinning with the aqueous phase.

In a twenty-seventh embodiment, the present invention provides a method as in any of the embodiments, wherein further comprising the step of collecting the poly(α-lipoic acid) polymer from the gas/water interface.

In a twenty-eighth embodiment, the present invention provides a method as in any of the embodiments, wherein, in the step of collecting, the poly(α-lipoic acid) polymer is collected as a filament.

In a twenty-ninth embodiment, the present invention provides a as in any of the embodiments, wherein, in the step of collecting, the polymer is collected as a film.

In a thirtieth embodiment, the present invention provides a method as in any of the embodiments, wherein, in the step of collecting, an adherend is contacted with the poly(α-lipoic acid) polymer at the gas/water interface.

In a thirty-first embodiment, the present invention provides a method as in any of the embodiments, wherein, in the step of exposing, the aqueous phase is atomized and deposited on the α-lipoic formulation.

In a thirty-second embodiment, the present invention provides a method as in any of the embodiments, wherein the aqueous phase is atomized and deposited by a 3-D printing device.

DETAILED DESCRIPTION OF ILLUSTRATIVE EMBODIMENTS

The present invention demonstrates a polymerization of α-lipoic acid proceeding at an gas/water interface, thus providing a truly green synthetic method of preparing poly (α-lipoic acid) polymers. The process can use any organic solvent miscible with water, including ethanol. Additionally, the resulting polymer requires no further purification as any residual monomer is a healthy, vital nutrient. This new method is useful not just for polymerization of bulk polymers, but also in the synthesis of polymer fibers (Example 2) and biocompatible adhesives (Example 3, 4). Additionally, drugs may be incorporated (Example 5) for controlled release. The monomers or polymers may be further processed using methods known to the polymer manufacturing industry (Example 6) to make useful biomedical or consumer products.

The present invention provides a method for the polymerization of α-lipoic acid and α-lipoic derivatives. In this method, an α-lipoic formulation is exposed to a aqueous phase and a gaseous phase at a gas/water interface, and the α-lipoic formulation polyermizes at the gas/water interface to form a poly(α-lipoic) polymer. Herein, an "α-lipoic formulation" can be an α-lipoic solution or an α-lipoic liquid. An α-lipoic solution includes an α-lipoic solute selected from the group consisting of α-lipoic acids, α-lipoic acid based-derivatives, and combinations thereof in an appropriate organic solvent, wherein the organic solvent is miscible with water. An α-lipoic liquid is simply a flowable form of α-lipoic acids, α-lipoic acid based-derivatives, and combinations thereof. In some embodiments, the α-lipoic liquid is simply the melt state of α-lipoic acids, α-lipoic based-derivatives, and combinations thereof.

In some embodiments employing an α-lipoic solution, the organic solvent is selected from the group consisting of ethanol, isopropanol, methanol, acetone, glycerin, propylene glycol, tetraethylene glycol, dioxane, dimethylsulfoxide and tetrahydrofuran. In some embodiments, the α-lipoic solution may also include oligomers or polymers of α-lipoic acid and/or α-lipoic acid derivatives.

In some embodiments wherein the α-lipoic formulation is an α-lipoic liquid, the α-lipoic liquid can further include oligomers or polymers of α-lipoic acid and/or α-lipoic acid containing compounds. In some embodiments, the α-lipoic liquid is liquid due to being heated to melt the crystalline state of the α-lipoic acids, α-lipoic acid based-derivatives, oligomer and polymers, according to what species are employed.

In a simple form, the α-lipoic formulation is exposed to an aqueous phase and a gaseous phase at a gas/water interface by depositing the α-lipoic formulation on and aqueous system. An aqueous system, as used herein, can entail water alone or a water-based liquid. The aqueous system provides a surface that is exposed to a gas to provide the gas/water interface.

In some embodiments, this gas will simply be air. In other embodiments, the gas may be an inert gas. In other embodiments, the gas is pure oxygen. In other embodiments, the aqueous phase may be provided by water, deionized water, water-based solutions, plasma, saliva, buffered solutions and other aqueous solutions. In some embodiments, the aqueous phase is provided by plasma present at a wound.

In some embodiments, the aqueous phase contains a water-soluble compound. In some embodiments, this water-soluble compound is a therapeutic agent. In some embodiments, the therapeutic agent is selected water soluble analgesics, acetylsalicylic acid, water soluble vitamins, ascorbic acid, water soluble antibacterial agents, sulfonamides and neomycin B. In other embodiments, the therapeutic agent is selected from the group consisting of acetylsalicylic acid, ascorbic acid, sulfonamides and neomycin B. In some embodiments, the water soluble compound is a drug for delivery to a patient.

In some embodiments, the α-lipoic formulation further includes a non-water soluble compound. In some embodiments, this non-water soluble compound is a therapeutic agent. In some embodiments, this water-soluble compound is a therapeutic agent. In some embodiments, the therapeutic agent is selected from the group consisting of curcumin, vitamins A, D, E or K, and 4(5-cyclopentyloxy-carbonylamino-1-methyl-indol-3ylmethyl)-3-methoxy-N-o-tolylsulfonylbenzamide (e.g. Zarfirlucast™). In some embodiments, the water soluble compound is a drug for delivery to a patient.

Although a simple form the method herein simply requires depositing an α-lipoic formulation on water so as to expose the α-lipoic formulation to an aqueous phase and a gaseous phase at a gas/water interface, the exposure to an aqueous phase and gaseous phase at a gas/water interface can be achieved through other methods. In some embodiments, the step of exposing is achieved by depositing the α-lipoic formulation onto a substrate surface having water thereon. In some embodiments, deposition may occur by syringe, by atomize spray, by electrospraying, by electrospinning, and by 3-D printing of the α-lipoic solution or α-lipoic liquid onto the gas/water interface.

Only a slight amount of water is needed and it has been found that the moisture on beakers and the like has been sufficient to achieve an appropriate gas/water interface. In some embodiments, water formed during reaction has been sufficient (see Example 7).

Figure 2:
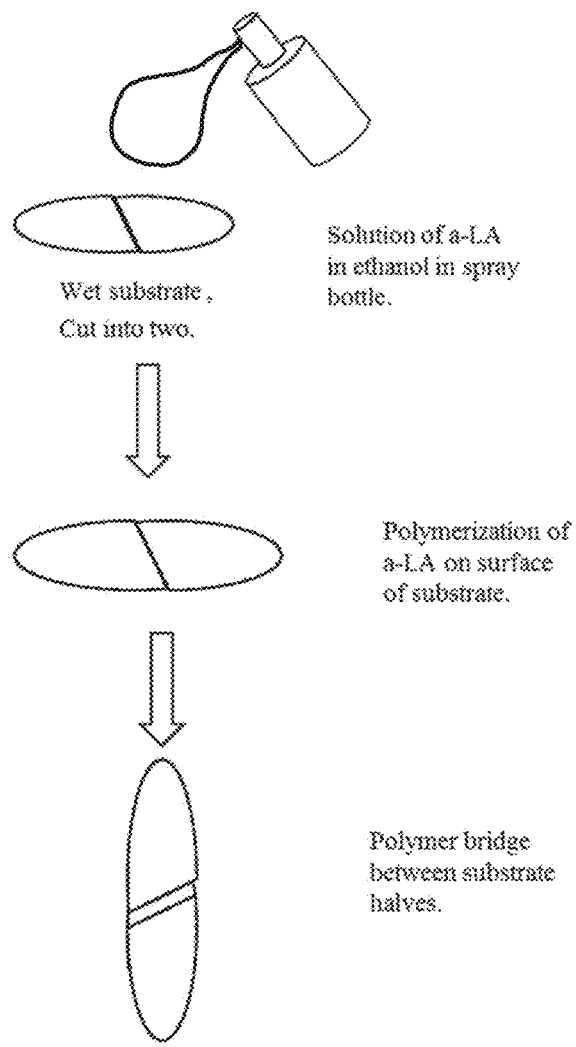
FIG. 2 is a schematic illustration of and adhesion technique wherein the α-lipoic formulation is deposited onto two surfaces separated from each other by a gap, each surface having water thereon.

In some embodiments, as seen in FIG. 2, the α-lipoic formulation is deposited onto two surfaces separated from each other by a gap, each surface having water thereon, and, when the α-lipoic formulation polymerizes the poly(α-lipoic acid) polymer that is formed bridges the gap and helps to hold the two surfaces in proximity to each other. These two surfaces could be skin surfaces at a wound site such as a cut or flap of skin.

In some embodiments, the α-lipoic formulation is atomized and deposited onto the gas/water interface, whether provided by a mass of water of water-coated surfaces. In some embodiments, the α-lipoic formulation is atomized and deposited by a 3-D printing device.

In some embodiments, the α-lipoic formulation is exposed to gas/water interface by being electrosprayed or electrospun onto a gas/water interface. In some embodiments, such as that shown in FIG. 6, the α-lipoic formulation is subjected to coaxial electrospinning wherein the spinnerette holds both the α-lipoic formulation and the aqueous phase in coaxial chambers, such that the two materials are drawn from the spinnerette toward a collection plate or collection bath (with a gas/water interface) and the α-lipoic formulation contacts the aqueous phase thus creating a gas/water interface during the electrospinning process and polymerizing as the materials are spun. The α-lipoic formulation then polymerizes during electrospinning and collection on the collection plate of the electrospinning process. If a collection bath is used, further polymerization will occur at the gas/water interface provided thereby.

In some embodiments, the aqueous system is deposited onto the α-lipoic formulation. The same methods can be employed, but the material being deposited is reversed. Thus, in some embodiment, the aqueous system can be deposited by syringe, by atomize spray, by electrospraying, by electrospinning, and by 3-D printing of the aqueous system onto an α-lipoic solution or α-lipoic liquid to create the gas/water interface.

It will be appreciated that use of the term "water" herein is to entail either water ($H_2O$) itself or aqueous systems (water-based liquids) and thus, the aforementioned plasma is also considered to provide "water" inasmuch as plasma is formed of a significant amount of water.

Figure 1:
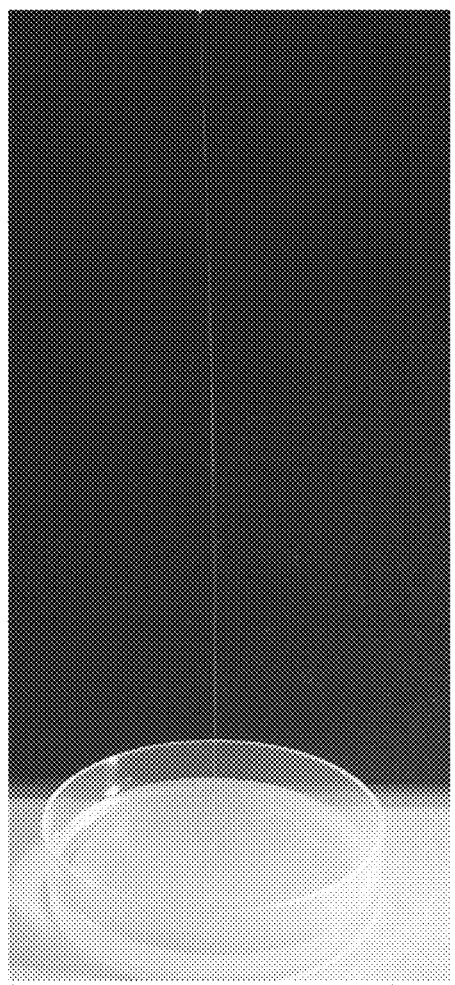
FIG. 1 is a photograph showing proof of the method of forming filaments (fibers) by pulling filaments of poly(α-lipoic acid) from the polymer formed at a gas/water interface.

In some embodiments, the aqueous phase providing the gas/water interface is evaporated to leave behind the poly (α-lipoic acid) polymer for collection. In other embodiments, the poly(α-lipoic acid) polymer is collected as a filament by contacting the polymer at the air/water interface and pulling it away from that interface, as generally shown in FIG. 1 and described in Example 2.

In some embodiments, the poly(α-lipoic acid) polymer can serve as an adhesive for adherends. An adherend can simply be contacted with the poly(α-lipoic acid) polymer at the air/water interface, the adherend thereby picking up some polymer on its surface. This surface can then be pressed against another surface to thereby adhere the adherend to that surface. In some embodiments, it is found that the surfaces to be adhered together can both be coated with the poly(α-lipoic acid) polymer to provide an even stronger adhesion. This is generally addressed in Example 3.

In some embodiments, multifunctional (bi, tri, and poly-functional) α-lipoic acids and α-lipoic acid based-derivatives can be employed as crosslinkers. In these embodiments, multifunctional α-lipoic acid derivatives or α-lipoic acid based-derivatives are employed with α-lipoic acid monomers, oligomers or polymers and permitted to polymerize therewith at the air/water interface. The multi-functional α-lipoic acids and/or α-lipoic acid based-derivatives link polymer chains through disulfide bonds, creating a cross linked gel. In some embodiments, this cross linking can occur during the creation of the bifunctional α-lipoic acid and/or α-lipoic acid based-derivatives, by synthesizing the multifunctional acids through esterification reactions with glycols. This is generally addressed in Example 7.

In light of the foregoing, it should be appreciated that the present invention significantly advances the art by providing methods for polymerization of α-lipoic acid and α-lipoic acid derivatives improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Both enantiomers of α-lipoic acid and mixtures thereof (CAS #1077-28-7, #1077-27-6, #1200-22-2) are biocompatible and used in the methods presented here. It will be appreciated that α-lipoic acid includes an R form and S form, and reference herein to R Example 1

Polymerization of R-α-LA at Air/Water Interface

A 0.500 M solution of α-LA in tetrahydrofurane (THF) was prepared. Using a syringe, 0.50 mL of the solution was dropped onto the surface of deionized water at three temperatures (25, 65 and 100° C.). The off-white products which formed at the air/water interface was collected and dried in a vacuum oven. These samples are named by the enantiomer of the α-lipoic acid (here the R form) and by the temperature of the water, with PPTN being an abbreviation of precipitation. For instance, sample R-PPTN-65, was formed by precipitating a solution of R-α-lipoic acid onto the surface of water held at 65° C. The conversion of each reaction is shown in Table 1.

TABLE 1

Yield and conversion data for the three precipitation polymers.

| Sample | Deionized H$_2$O Temp (C.) | Mass Product (g) | % Conv. of α-LA |
|---|---|---|---|
| R-PPTN-25 | 25 | 0.0279 | 47.9 |
| R-PPTN-65 | 65 | 0.0241 | 41.3 |
| R-PPTN-100 | 100 | 0.0218 | 37.4 |

In the size exclusion chromatography (SEC) analysis, polymers were dissolved in THF and filtered through a 0.45 μm polytetrafluoroethylene (PTFE) filter. R-PPTN-100 went through the filter without difficulty. R-PPTN-65 was more difficult to push through the filter, and sample R-PPTN-25 was the most difficult. The results from R-PPTN-65 and R-PPTN-100 are shown in Table 2. SEC data for R-PPTN-25 is not available because not enough polymer remained in solution after sample preparation, and refractive index (RI) signals were very weak.

SEC traces for R-PPTN-65 and R-PPTN-100 showed that, in addition to the peak in the high molecular weight region, both SEC traces had large peaks in the low molecular weight region of the chromatogram. The high molecular weight products from R-PPTN-65 and R-PPTN-100 reached Mn well over 1,000,000 g/mol, which was the upper detection limit of the instrument.

TABLE 2

SEC data for polymers synthesized by precipitation (dn/dc = 0.109 mL/g).

| Sample | $M_n$ (g/mol) | $M_w$ (g/mol) | $M_w/M_n$ | $R_{gz}$ (nm) | $R_{hw}$ (nm) | $[\eta]_w$ (mL/g) |
|---|---|---|---|---|---|---|
| R-PPTN-65 | 2,672,000 | 3,414,000 | 1.28 | 92.0 | 56.6 | 354.7 |
| R-PPTN-100 | 4,207,000 | 4,583,000 | 1.09 | 111.5 | 69.8 | 489.4 |

Example 2

Filament Formation

As described here previously, poly(α-LA) forms at the air/water interface. During this process, it is also possible to create polymer filaments which are pulled from the interface. FIG. 1 shows a polymer fiber pulled from the same system used in R-PPTN-25 Sample of Example 1.

Example 3

Poly(α-LA) Biocompatible, Anti-Oxidant Adhesive

Poly(α-LA) forms a powerful adhesive with a variety of substrates including, but not limited to: itself, nanofibers, cellulose, skin and other protein-based substrates. To make the adhesive, α-LA was precipitated onto water, as described in Example 1, then the substrates (in this example SIBS nanofiber mats) were held firmly and "rolled" or "rocked" on top of the polymer at the air-water interface. The polymer adhered to both pieces of nanofiber mat. Then the nanofiber mats were pressed together at their respective poly(α-LA) coated surfaces for several seconds. The adhesion offered by the overlapping poly(α-LA) surfaces of these nanofiber mats (approx. 2.25 cm$^2$) was sufficient to hold a mass of approximately 200 g.

Example 4

Poly(α-LA) Biocompatible, Anti-Oxidant Adhesive Spray Adhesive

In this example, α-LA is polymerized directly onto a wet substrate. An ethanolic solution of α-LA was sprayed onto a wet substrate which was previously cut into two pieces. A bridge of poly(α-LA) connected the two pieces of the cut substrate. A cartoon of the procedure is shown in FIG. 2. This system could be particularly useful for wound healing applications as polymer itself would act to reduce further injury and inflammation from oxidative reactions that occur at wound sites. A cut or flap of skin at a wound, wherein the compromised skin provides edges in close proximity (e.g. from 0 to 10 mm), could be sprayed with water or other aqueous-based liquid and then the α-LA monomer deposited thereon (for example, by spraying), and the monomer would polymerize and bridge across the gap between the edges thus holding the wound together and providing protection. In other embodiments, this is practiced on a burn wound, where the polymerization of α-LA monomer (or its derivatives) would halt or inhibit harmful tissue oxidation thereby lessening the extent of burn damage. The poly(α-lipoic acid) formed at the burn site would also seal the wound from outside contaminants like bacteria. In other embodiments the α-lipoic acid spray and the polymer formed therein is a first-aid measure used for burns.

Example 5

Poly(α-LA) Biocompatible, Anti-Oxidant Drug-Eluting Polymer

Curcumin is also a powerful anti-oxidant that is recommended in the treatment of neural and memory disorders. However, its uptake is severely limited by its hydrophobicity. Here it serves as a model compound representing any hydrophobic drug. In this example α-LA was dissolved in ethanol with curcumin. The ethanolic solution was then dropped onto the surface of water as described in Example 1. When a fiber was pulled from this surface as described in Example 2, the fiber was a bright orange color, indicating that curcumin was readily incorporated into the polymer. Through degradation back to the original monomer, a necessary nutrient, the curcumin (or other drug, as curcumin is employed herein as a proof of concept) would be released.

Example 6

Compression Molding of α-LA into Polymeric Products

This example demonstrates the physical properties of poly(α-LA), and it demonstrates the rate of degradation under biological conditions. Powdered polymer feedstock is often used in industrial manufacturing methods, like injection and compression molding. For example, a powdered polymer feedstock may be added to the hopper of an injection molding machine, melted and then used to fill the mold cavity. Alternatively, the polymers made in Examples 1, 2, or 5 could be powdered and used as feed stock. This example demonstrates the physical properties of various samples of compression molded poly(α-LA) and degradation under biological conditions. These samples are named by the enantiomer of the α-lipoic acid (with R indicating the R form thereof and DL indicating a mixture of the R form and S form thereof) and by the molding temperature, with CM being an abbreviation for compression molding.

TABLE 3

Molding conditions for α-LA monomers and observations.

| Sample | Molding Temp (° C.) | Time | Annealed | Observations of |
|---|---|---|---|---|
| DL-CM-95 | 95 | 2 hrs | Yes | Opaque pale yellow with holes |
| DL-CM-90 | 90 | 2 hrs | Yes | Opaque pale yellow |
| R-CM-100 | 100 | 5 min | No | Transparent bright yellow |
| R-CM-90 | 90 | 2 hrs | Yes | Transparent yellow with opaque patches |

Compression molding of DL-α-LA at 95° C. produced an opaque, pale yellow polymer sheet (sample name DL CM 95). The sample showed several holes in the otherwise

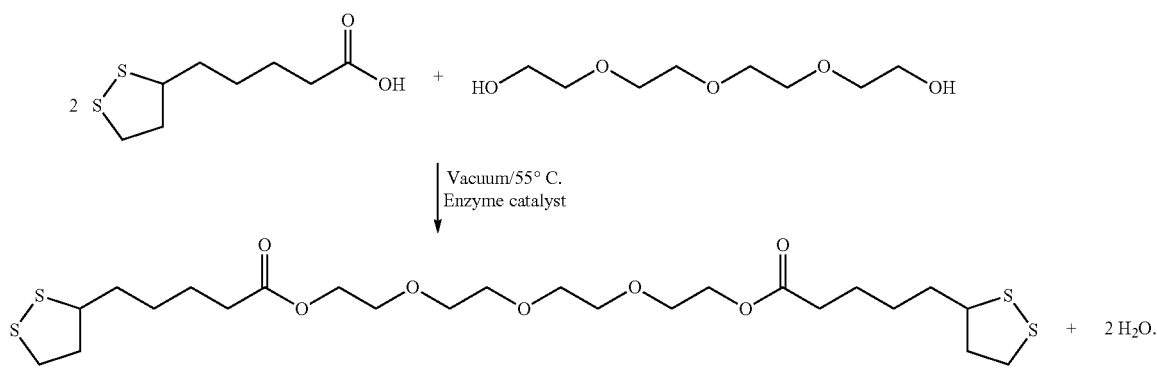

smooth, tough sheet. To avoid sheet defects in subsequent compression molding trials, the monomers were melted thoroughly in the mold before placing them in the compression press. Sample R-CM-90 (A) was tough, smooth and not sticky. Sample R-CM-90 (B) was perfectly transparent when it was removed from the mold, but opaque regions grew after 3 days. The sample was slightly sticky and had an elastic give when touched.

Figure 3:
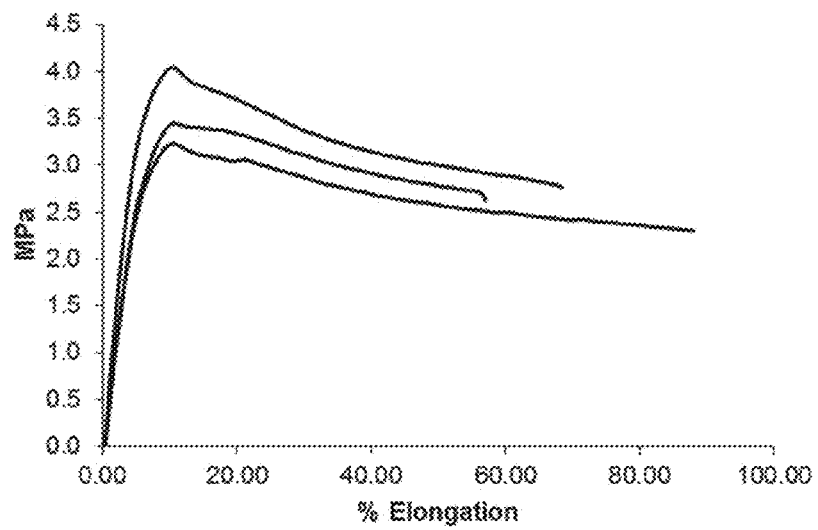
FIG. 3 is a graph of the tensile curves of DL-CM-95 in Example 6 herein.

The tensile curves from DL-CM-95 are shown in FIG. 3. Three micro tensile bars were die-cut from the molded sheet, measured, and pulled on a tensiometer at an extension 500 mm/min at room temperature. Showed a Young's modulus is 0.066 GPa and the highest ultimate tensile strength reached (UTS) was 4.02 MPa. The average UTS of the three measurements was 3.55 MPa. Because sample DL-CM-95 was opaque, it was not possible to see any internal defects.

Figure 4:
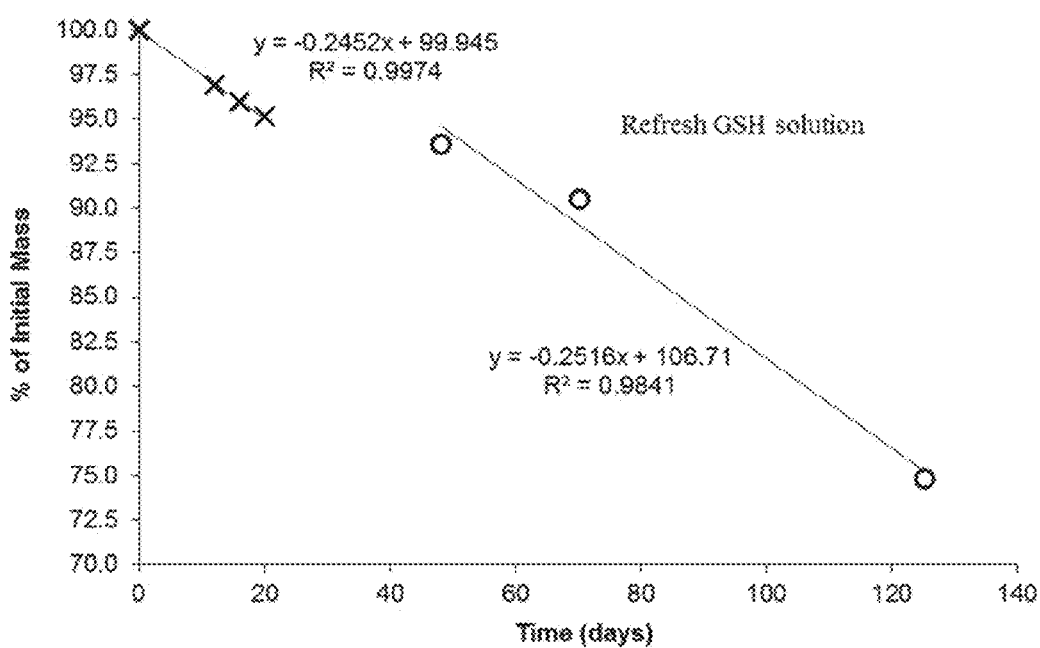
FIG. 4 is a plot of sample mass loss with time from Example 6 herein.

A sample of DL-CM-95 was placed in 50 mM GSH in sodium acetate buffer solution (pH=5.2) and incubated at 37° C. A plot of sample mass loss with time is shown in FIG. 4. Degradation appeared to slow after 21 days, and fresh GSH solution was added. From the slope of the lines, complete degradation after 400-425 days was calculated.

When sample DL-CM-95 was incubated with aqueous GSH at 37° C. it became transparent. When a small sample of DL-CM-95 was placed in the oven alone and it also became translucent. The loss of opacity was thought to indicate a loss of crystallinity. Because crystallinity often adds strength to elastomers, the tensile strength of compression molded α-LA was tested at 37° C.

Figure 5:
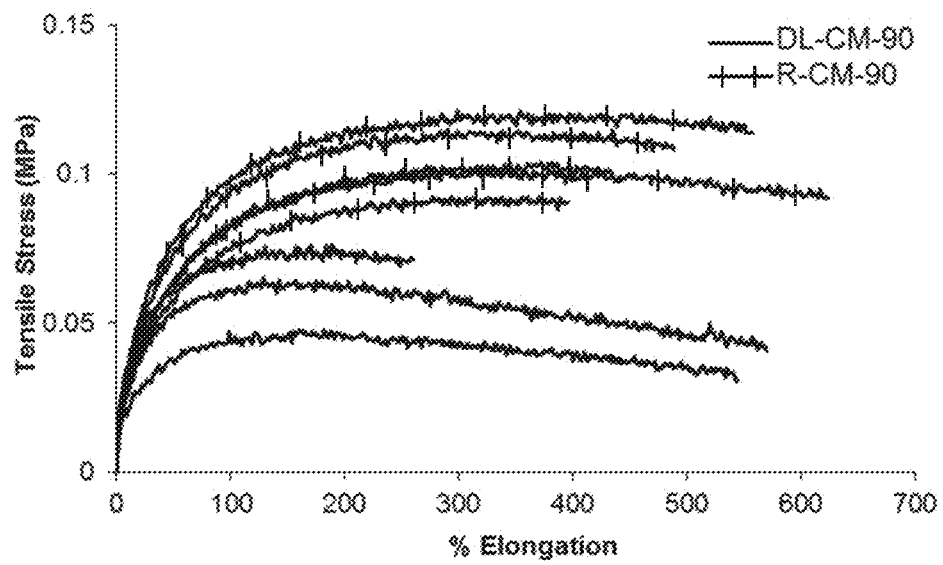
FIG. 5 is a graph of the tensile curves from DL-CM-90 and R-CM-90 in Example 6 herein.

The tensile curves from DL-CM-90 and R-CM-90 are shown in FIG. 5. The samples were measured on a tensiometer with a temperature-control chamber set to 37° C. Sample DL-CM-90 showed an UTS of 0.060 MPa (average of 3 measurements), while R-CM-90 had a UTS of 0.105 MPa (average of 5 measurements). The tensile properties of compression molded DL-α-LA at 37° C. are much lower than at room temperature.

Example 7

Crosslinked Poly(α-LA) Materials

In this example a bifunctional α-LA derivative was synthesized and used to form a crosslinked α-LA-based material. The bifunctional α-LA derivative was synthesized in a double esterification reaction of tetraethylene glycol (TEG) with α-LA in a 1:2 molar ratio, as below:

In a Schlenk tube equipped with a stir bar 1 mL TEG (0.0057 mol), 2.3811 g (0.0115 mol) α-LA and 60 mg enzyme catalyst were added. The Schlenk tube was then placed in an oil bath thermostated at 55° C. and placed under vacuum. Because water is produced as a reaction product and the α-LA polymerizes at an air/water interface, polymerization occurs even as the bifunctional α-LA derivative is formed. Thus, a sticky yellow mass formed indicating partial polymerization. The product was dissolved in THF and filtered to remove the enzyme catalyst. Upon solvent removal, resulting product was a crosslinked gel, wherein the bifunctional α-LA links polymer chains through disulfide bonds. Esterification and polymerization reactions were performed simultaneously. The crosslinked product was further purified by extraction of in THF followed by $H_2O$. It swelled in THF and turned white in water indicating the extraction of free α-LA.

To demonstrate the crosslinking, a portion of the network was swollen to equilibrium in THF. The network gained over 700% its original mass. Data from the swelling study are given below.

Dry mass: 0.0798 g

Swollen mass: 0.6450 g

Mass gain (aka. mass THF): 0.5652 g

% Mass gain: 708%

The crosslinking can be important because it increases the strength of the polymer, which generally loses strength above temperatures of about 37° C., the temperature experienced in applications in or on the human body. Thus achieving this crosslinking can be important in making sutures, medical meshes and the like.

Example 8

Electrospun Fibers Poly(α-LA) Via Melt Electrospinning

In this example, poly(α-LA) melt is subjected to the fiber forming technique of melt electrospinning which creates microscale to nanoscale fibers. A standard melt electrospinning technique and apparatus was employed. The crystalline monomer is heated above its melting point which induces partial polymerization and will be referred to as the oligomer melt. These samples are named by the enantiomer of the α-lipoic acid (with R indicating the R form thereof and DL indicating a mixture of the R form and S form thereof). Experimental results showed that R-α-LA displays a melting point onset of 47.35° C. with a melting peak of 49.45° C., while DL-α-LA showed a melting point onset of 57.66° C. with a melting peak of 60.61° C. The results were in good agreement with literature values for both compounds. The oligomer melt, loaded in the syringe, was subjected to an electrical voltage to create the electrified jet which spins the fibers. Fibers were collected on a conductive surface (i.e. water, aqueous solution, metal plate, rotating drum, etc). Fibers collected on a surface having water thereon undergo further polymerization on contact. Fibers which are not collected on an aqueous surface may be later treated, for example by exposure to an air-water interface, or by exposure to an oxidizing agent like aqueous hydrogen peroxide, to reach higher degrees of polymerization. The spinning and collection portions of the apparatus may be encased in a non-conductive temperature controlled chamber to prevent recrystallization of the monomer melt. Experiments with compression molded polymerization (Example 6) indicated that recrystallization is prevented at temperatures below the melting temperature (eg 37° C.).

Example 9

Electrospun Fibers Poly(α-LA) Via Melt Electrospinning

Figure 6:
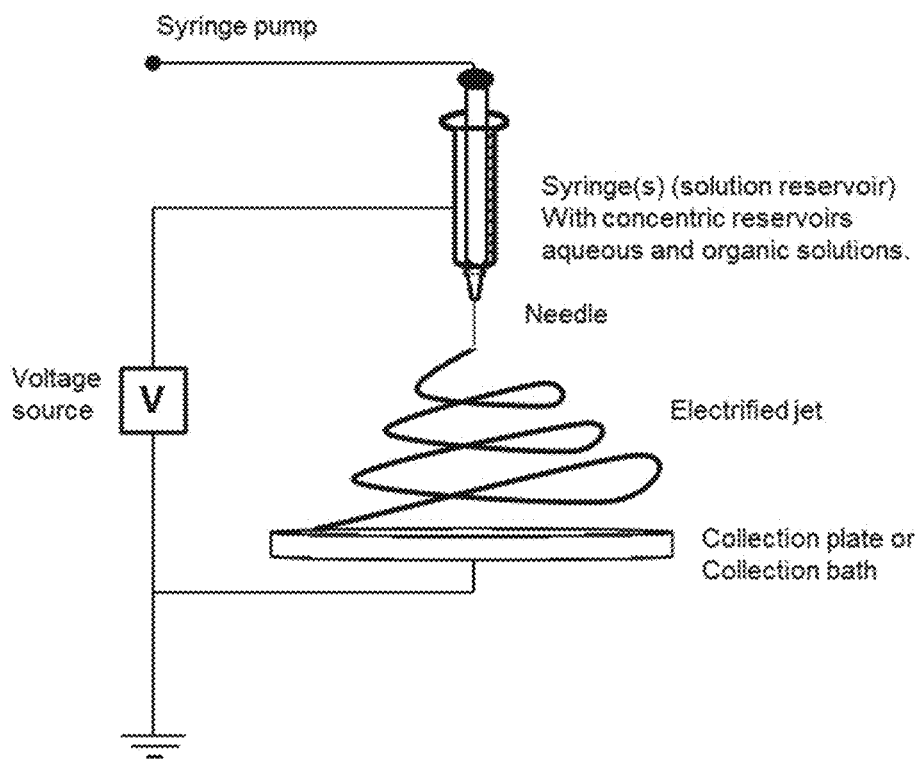
FIG. 6 is a schematic illustration of a coaxial electrospinning apparatus used to expose the α-lipoic formulation to a gas/water interface.

In this example, α-LA (or derivatives including oligomers or polymers of α-LA) solution was subjected to the fiber forming technique of coaxial electrospinning which creates microscale to nanoscale fibers. A standard coaxial electrospinning technique and apparatus was employed and is shown in FIG. 6. Here the α-LA (or derivative) organic solution and aqueous solution are confined in concentric reservoirs and meet in the Taylor cone of the electrospinning apparatus. In light of the presence of water and thus an air/water interface, polymerization occurs as the electrified jet is pulled toward the conductive collection stage. Fibers are collected on a conductive surface (i.e. water, aqueous solution, metal plate, rotating drum, etc). Fibers which are collected onto an aqueous or damp surface undergo further polymerization on contact. Fibers which are not collected on an aqueous surface maybe later treated, for example by exposure to an air-water interface, or by exposure to an oxidizing agent like aqueous hydrogen peroxide, to reach higher degrees of polymerization.

What is claimed is:

1. A method of forming filaments from the polymerization of α-lipoic acid, the method comprising:
   providing a liquid α-lipoic formulation in the form of a solution of α-lipoic acids dissolved in an organic solvent miscible with water,
   exposing said liquid α-lipoic formulation to an aqueous phase and a gaseous phase at a gas/water interface;
   allowing the liquid α-lipoic formulation to polymerize in light of being present at the gas/water interface to form a poly(α-lipoic acid) polymer; and
   forming filaments by pulling filaments of said poly(α-lipoic acid) polymer formed at said gas/water interface.

2. The method of claim 1, wherein said organic solvent is selected from ethanol, isopropanol, methanol, acetone, glycerin, propylene glycol, tetraethylene glycol, dioxane, dimethylsulfoxide and tetrahydrofuran.

3. The method of claim 1, wherein the liquid α-lipoic formulation further includes a non-water soluble compound.

4. A method of claim 3, wherein the non-water soluble compound is selected from a therapeutic agent and a crosslinking agent.

5. The method of claim 1, wherein the aqueous phase contains a water-soluble compound.

6. The method of claim 5, wherein the water soluble compound is a therapeutic agent.

7. The method of claim 1, wherein the gaseous phase is selected from air, an inert gas, and pure oxygen.

8. The method of claim 1, wherein, in said step of exposing, said liquid α-lipoic formulation is deposited onto water.

9. The method of claim 8, wherein, in said step of exposing, the liquid α-lipoic formulation is deposited onto a substrate surface having water thereon.

10. The method of claim 1, wherein, in said step of exposing, the liquid α-lipoic formulation is electrosprayed or electrospun onto a gas/water interface.

11. A polymerization method for forming filaments comprising:
    providing a liquid formulation consisting of α-lipoic acid dissolved in an organic solvent miscible with water,
    exposing the liquid formulation to an aqueous phase and a gaseous phase at a gas/water interface;
    allowing the exposed liquid formulation to polymerize to form a polymer comprising poly(α-lipoic acid), where the polymerization occurs in light of being present at the gas/water interface; and
    forming filaments by pulling filaments of the polymer formed at the gas/water interface.

* * * * *